(12) United States Patent
Deng

(10) Patent No.: US 9,144,617 B2
(45) Date of Patent: Sep. 29, 2015

(54) METHOD OF DISINFECTION AND LIGHTING BY USING LEDS AND LED DEVICE THEREOF

(71) Applicant: Weizeng Deng, Hongkong (CN)

(72) Inventor: Weizeng Deng, Hongkong (CN)

(73) Assignee: GUANGDONG LIGHT COLLECTION TECHNOLOGY COMPANY LIMITED, HK (CN)

( * ) Notice: Subject to any disclaimer, the term of this patent is extended or adjusted under 35 U.S.C. 154(b) by 0 days.

(21) Appl. No.: 14/164,163

(22) Filed: Jan. 25, 2014

(65) Prior Publication Data

US 2014/0299793 A1    Oct. 9, 2014

(30) Foreign Application Priority Data

Apr. 9, 2013  (CN) .......................... 2013 1 0123739

(51) Int. Cl.
 *A61N 5/06* (2006.01)
 *G01J 3/10* (2006.01)
 *H05G 2/00* (2006.01)
 *A61L 2/10* (2006.01)

(52) U.S. Cl.
 CPC ........................................ *A61L 2/10* (2013.01)

(58) Field of Classification Search
 USPC ..................... 250/504 R; 433/29, 91, 93, 140
 See application file for complete search history.

(56) References Cited

U.S. PATENT DOCUMENTS

2008/0194054 A1*  8/2008  Lin et al. .......................... 438/64
2010/0190129 A1*  7/2010  Paz ................................. 433/29

* cited by examiner

*Primary Examiner* — David Porta
*Assistant Examiner* — Meenakshi Sahu

(57) ABSTRACT

A method of disinfection and lighting by using LEDs and an LED device thereof are provided. Two kinds of LEDs, i.e., the lighting LEDs, and the UV-LEDs, are fixed on a circuit board evenly and mixedly in a certain way, and a separator is also provided on the circuit board. Meanwhile, a controlling circuit module having a function of mode switching controls the UV-LEDs and the lighting LEDs, in such a manner that the functions of UV-LED disinfection and LED lighting are combined well in a same device. The method replaces a conventional method of sterilization and disinfection using ultraviolet (UV) rays emitted by a low pressure mercury vapor lamp. After being treated with light distribution by the separator, directionality of light emitted by the LED is stronger, and the LED is easier to operate.

9 Claims, 3 Drawing Sheets

METHOD OF DISINFECTION AND LIGHTING BY USING LEDS AND LED DEVICE THEREOF

BACKGROUND OF THE PRESENT INVENTION

1. Field of Invention

The present invention relates to a field of light emitting diode (LED) electronic lighting, and more particularly to a method of disinfection and lighting by using LEDs and an LED device thereof.

2. Description of Related Arts

In conventional technology, low pressure mercury vapor lamps emit ultraviolet rays to realize functions of sterilization and disinfection. The low pressure mercury vapor lamp comprising the quartz tube has disadvantages of high energy consumption, short service life, big size, being easy to damage, requiring special power supply, long starting period, etc. The application of the low pressure mercury vapor lamp is limited in the medical field, and it is hard to apply the low pressure mercury vapor lamp in more fields. In addition, the mercury in the low pressure mercury vapor lamp pollutes the environment easily. As a new lighting source, the light emitting diode, i.e., LED, overcomes many shortcomings of conventional light sources, and has many advantages of low energy consumption, long service life, small size, being sturdy and durable, simple driving power, being capable of starting quickly and frequently, etc. The LED has been widely applied in many fields, wherein the visible LED is applied the most widely. The energy band structure of quantum well in the LED may be adjusted, in such a manner that the LED emits light of various wavelengths. The ultraviolet light emitted by the conventional sterilizing lamp is replaced by the ultraviolet light emitted by the LED, which is a significant progress in the field of disinfecting device. In the Chinese patent having an application number of 201120023893.3, the visible LED is combined with the ultraviolet LED, and an LED light source having composite functions of lighting and sterilization and disinfection is manufactured. The ultraviolet rays emitted by the LED in the patent have a remarkable effect of sterilization and disinfection on the air. However, the strong ultraviolet light emitted has not been treated effectively in the patent, and the radiation of the strong ultraviolet light is full of the space. Thus, the strong ultraviolet rays will hurt eyes and skin of people, when the LED is not used correctly. When the ultraviolet rays are used to disinfect things, people must be away from the scene. Thus, the air cannot be disinfected timely to prevent some diseases from spreading by air. In addition, the LED for lighting sealed in the same device is also damaged by the strong ultraviolet, and the service life of the LED for lighting is shortened. The ideal effect can not be achieved, and many inconveniences in disinfection and lighting are brought to users.

SUMMARY OF THE PRESENT INVENTION

In order to overcome shortcomings of the above conventional technology, the present invention provides a method of disinfection and lighting by using LEDs and an LED device thereof. The method replaces a conventional method of sterilization and disinfection by using ultraviolet (UV) rays emitted by a low pressure mercury vapor lamp. A lighting LED and a UV-LED is combined in the present invention to manufacture the LED device having composite functions of lighting and disinfection. A light source of the LED device is easier to operate. The LED device has a higher safety factor, and the lighting LED has a longer service life.

The method of disinfection and lighting by using LEDs is as follows. Two kinds of LEDs, i.e., the lighting LEDs, and the UV-LEDs, are fixed on a circuit board evenly and mixedly in a certain way, and a separator is also provided on the circuit board. Strong UV light emitted by the UV-LEDs and illumination light emitted by the lighting LEDs are separated and treated with light distribution of orientation by the separator. Meanwhile, a controlling circuit module having a function of mode switching controls the UV-LEDs and the lighting LEDs. A user operates the controlling circuit module to switch to a UV mode or a lighting mode, in such a manner that disinfection or lighting is executed by the LED device. In a first working mode, only the lighting LEDs work. In a second working mode, only the UV-LEDs work. In a third working mode, the lighting LEDs and the UV-LEDs work simultaneously. The user operates the controlling circuit module to choose the working mode. The functions of UV-LED disinfection and LED lighting are combined well in a same device in aspects of hardware and circuit. The LED device comprises: a body, a shield, a cover, and a controlling circuit module, wherein the controlling circuit module is provided in a lower portion of the shield, the shield and a thread of the cover are provided on the body. The LED device further comprises a reflecting cup, provided on the circuit board, where the LEDs are welded. The reflecting cup is in a shape similar to an inverted trapezium, and comprises a plurality of reflecting cellular cups, which are arranged like a honeycomb. The reflecting cup comprises two kinds of reflecting cellular cups. For example, if a first kind of reflecting cellular cups in a center has a size of 1, a second kind of reflecting cellular cups around the first kind of reflecting cellular cups has a size of 0.1~0.9.

The LED in the present invention is a directional light source. After being treated with light distribution by the reflecting cup, directionality of light emitted by the LED is stronger, and the LED is easier to operate. No matter the LED is applied in a field of lighting, disinfection, or solidification, luminosity environment of the LED is not more than 180 degree. The UV-LEDs and the lighting LEDs are separated physically by the reflecting cup in the present invention, in such a manner that the light emitted by the LED device is homogeneous enough and has a strong directionality, so the strong UV light will not hurt people in some situations, and the lighting LEDs in the same LED device will not be hurt by the strong UV light. Therefore, the service life of the LED device is lengthened, and the two kinds of LEDs are combined in a same lamp. It is proved by experimental data that the service life of the lighting LEDs working in an environment without radiation of strong UV light is more than 5 times longer than the service life of the lighting LEDs working in an environment with radiation of strong UV light.

The LED device in the present invention is applicable in various situations requiring lighting or sterilization and disinfection on surfaces of objects or some liquid. Especially, in outdoor activities and in some random situation, the LED devices can be used to disinfect foods. As an important auxiliary light source, the LED device is an indispensable defending tool in the case of an unforeseen accident.

These and other objectives, features, and advantages of the present invention will become apparent from the following detailed description, the accompanying drawings, and the appended claims.

Figure 1:
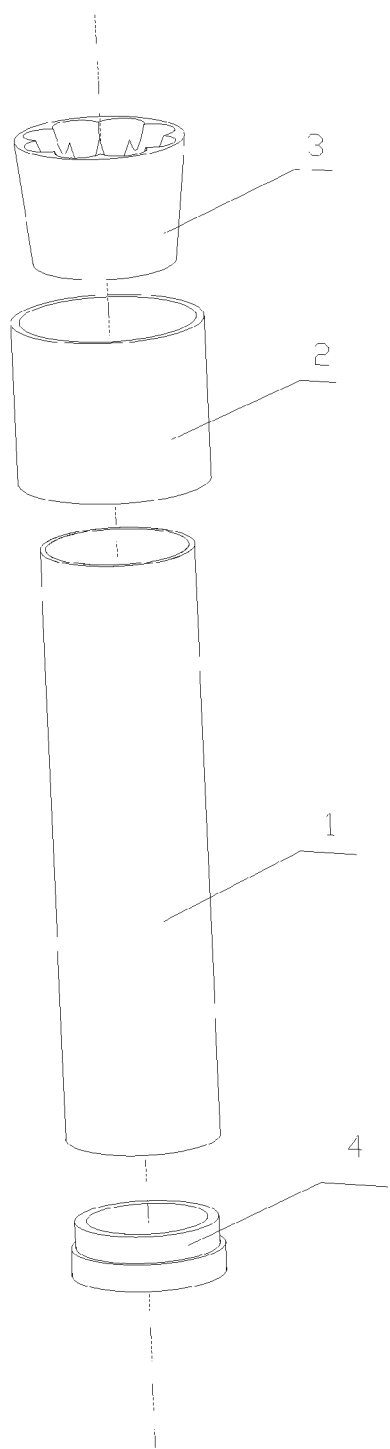
FIG. 1 is an exploded view of an LED device according a preferred embodiment of the present invention.

In the drawings, 1 refers to a body, 2 refers to a shield, 3 refers to a reflecting cup, 3a refers to a reflecting cellular cup in a center, 3b refers to reflecting cellular cups around the center, 4 refers to a cover, 5 refers to a controlling circuit module, 5a refers to a circuit board, and 6 refers to LED holes.

DETAILED DESCRIPTION OF THE PREFERRED EMBODIMENT

The method of disinfection and lighting by using LEDs is as follows. Two kinds of LEDs, i.e., the lighting LEDs, and the UV-LEDs, are fixed on a circuit board 5a evenly and mixedly in a certain way, and a separator is also provided on the circuit board 5a. Strong UV light emitted by the UV-LEDs and illumination light emitted by the lighting LEDs are separated and treated with light distribution of orientation by the separator. Meanwhile, a controlling circuit module 5 having a function of mode switching controls the UV-LEDs and the lighting LEDs. A user operates the controlling circuit module 5 to switch to a UV mode or a lighting mode, in such a manner that disinfection or lighting is executed by the LED device. In a first working mode, only the lighting LEDs work. In a second working mode, only the UV-LEDs work. In a third working mode, the lighting LEDs and the UV-LEDs work simultaneously. The user operates the controlling circuit module 5 to choose the working mode. The functions of disinfection and lighting are combined well in a same device in aspects of hardware and circuit. The LED device comprises: a body 1, a shield 2, a cover 4, and a controlling circuit module 5. The LED device further comprises a reflecting cup 3, provided on the circuit board 5a, where the LEDs are welded. The reflecting cup 3 is in a shape similar to an inverted trapezium, and comprises a plurality of reflecting cellular cups, which are arranged like a honeycomb. The reflecting cup 3 comprises two kinds of reflecting cellular cups. For example, if a first kind of reflecting cellular cups in a center has a size of 1, a second kind of reflecting cellular cups around the first kind of reflecting cellular cups has a size of 0.1~0.9.

The LED device in the present invention is further illustrated in detail according to the drawings.

Figure 2:
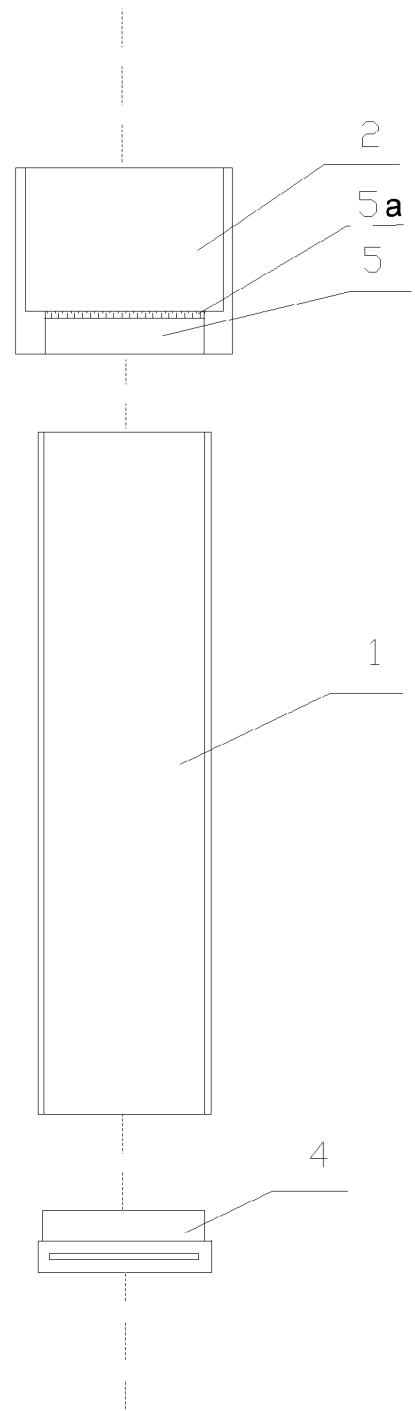
FIG. 2 is a vertical sectional view of some parts of the LED device according the preferred embodiment of the present invention.

Referring to FIG. 1 and FIG. 2, the LED device having composite functions of disinfection and lighting, comprises: the body 1, the shield 2, the cover 4, the reflecting cup 3, and the controlling circuit module 5, wherein the two kinds of LEDs, i.e., the lighting LEDs and the UV-LEDs, are fixed on the circuit board 5a, the controlling circuit module 5 and the reflecting cup 3 are assembled into the shield 2, and the shield 2 and the cover 4 are assembled on the body 1.

Figure 3:
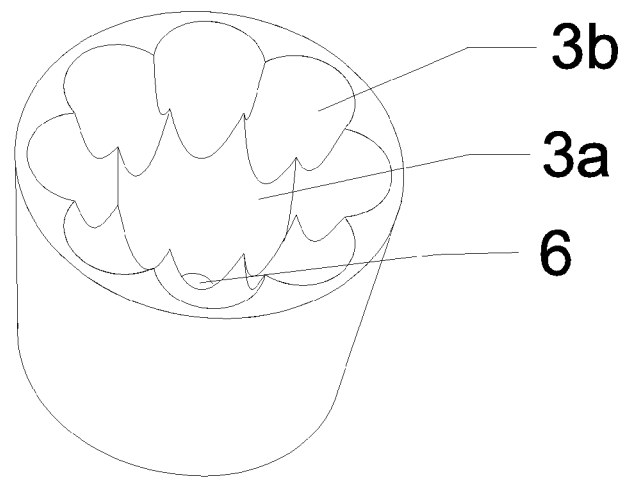
FIG. 3 is a perspective view of a reflecting cup of the LED device according the preferred embodiment of the present invention.
Figure 4:
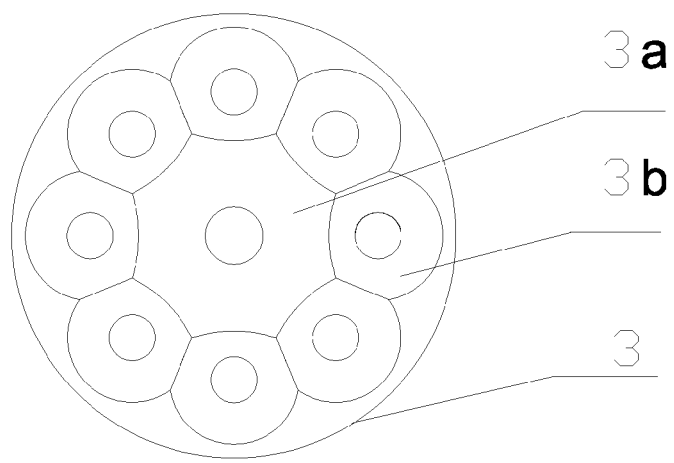
FIG. 4 is a top view of the reflecting cup of the LED device according the preferred embodiment of the present invention.
Figure 5:
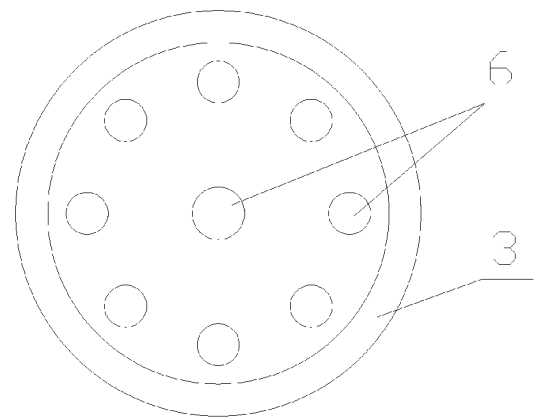
FIG. 5 is a bottom view of the reflecting cup of the LED device according the preferred embodiment of the present invention.

Referring to FIG. 3, FIG. 4, and FIG. 5, the reflecting cup 3 is in a shape similar to an inverted trapezium. The reflecting cup 3 comprises a plurality of reflecting cellular cups, which are arranged like a honeycomb. The LEDs welded on the circuit board 5a are respectively inserted into the corresponding reflecting cellular cups 3a or 3b, arranged like a honeycomb, through corresponding LED holes, wherein the reflecting cellular cups 3a in the center have a size bigger than the reflecting cellular cups 3b around the center have. The reflecting cellular cups 3b around the center are same in size, in such a manner that the LEDs in same type are treated by same light distributions, and light emitted by the LEDs are homogeneous. A height of the reflecting cup 3, diameters of the reflecting cellular cups 3a in the center, and diameters of the reflecting cellular cups 3b around the center are adjusted in proportion according to a size of the LED device. The diameters of the reflecting cellular cups 3a in the center, and the diameters of the reflecting cellular cups 3b are preset according to an actual optical effect and the size of the LED device. If a size of the reflecting cellular cups in the center is supposed as 1, the size of the reflecting cellular cups around the center is 0.1~0.9. The UV-LEDs are inserted into the reflecting cellular cups 3a in the center, in such a manner that the reflecting cellular cups 3a in the center distribute light of the UV-LEDs, and the reflecting cellular cups 3b around the center distribute light of the lighting LEDs. According to actual situation, the reflecting cellular cups 3b around the center distribute the light of the UV-LED, and the reflecting cellular cups 3a in the center distribute the light of the lighting LEDs.

Figure 6:
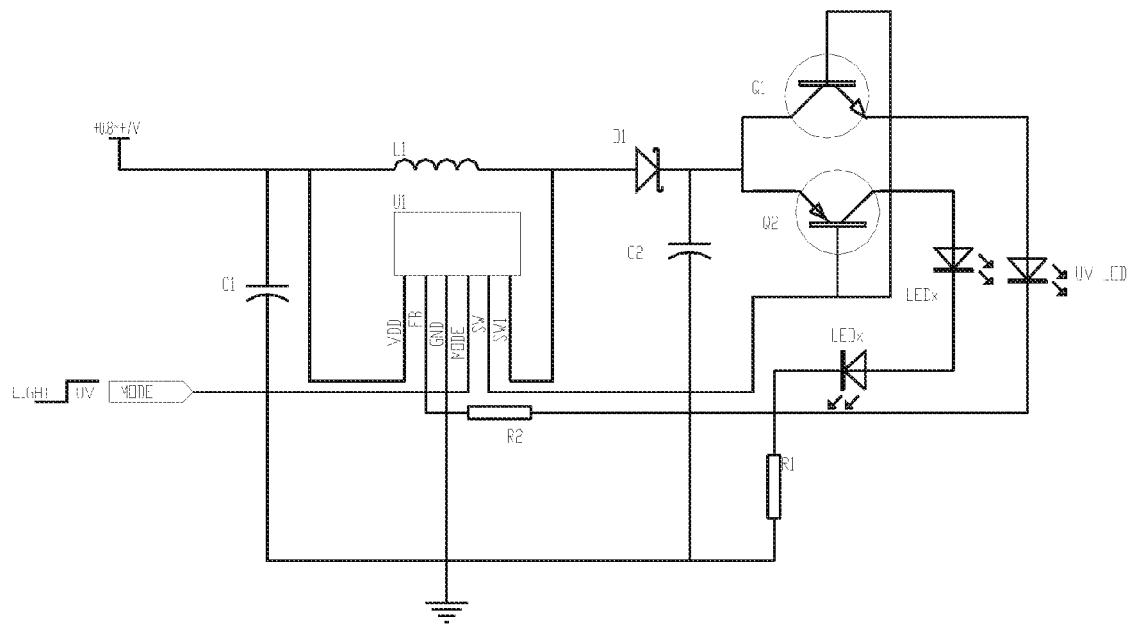
FIG. 6 is a diagram of controlling circuit according the preferred embodiment of the present invention.

Referring to FIG. 6, LEDx in a diagram of a controlling circuit refers to the lighting LED. UV-LED is for disinfection. The controlling circuit module comprises a mode allowance switch MODE, for switching to a UV MODE for disinfection or a LIGHT MODE for lighting. The controlling circuit module is operated according to operating steps as follows. a) For lighting, MODE is switched to the LIGHT MODE, and then the controlling circuit starts the lighting mode, wherein LEDx works, and UV-LED stops working. b) For disinfection, MODE is switched to the UV MODE, and then the controlling circuit starts a disinfection mode, wherein UV-LED works, and LEDx stops working. c) When the composite functions of lighting and disinfection are required, MODE is switched to the UV MODE. Terminal SW1 outputs a certain power by a built-in circuit in U1. N-type diode Q1 and P-type diode Q2 are selectively electrified by time division method, in such a manner that LEDx and UV-LED works alternately. Because gating frequency is high, naked eye is not able to perceive switching of working state of LEDx and UV-LED. In using effect, LEDx and UV-LED works simultaneously. In the UV MODE, step b) or step c) is executed. In the LIGHT MODE, only step a) is executed.

The present invention is to protect a method of disinfection and lighting by using LEDs and an LED device thereof, which comprises the separator for separating the LEDs having different wavebands, and assembling the LEDs; and the controlling circuit module having composite functions of UV-LED disinfection and LED lighting. A handheld LED device in the above embodiment is just taken as an example to further describe technology of the present invention and help readers to understand the present invention more easily. One skilled in the art will understand that the embodiment of the present invention as shown in the drawings and described above is exemplary only and not intended to be limiting. For example, shapes of the reflecting cup and the reflecting cellular cups can be changed into roundness, square, hexagon, polygon, or etc. Size proportion of the reflecting cellular cups can be changed. The LED device can be a non-handheld device.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method of disinfection and lighting by using LEDs, comprising: fixing two kinds of LEDs, i.e., lighting LEDs, and UV-LEDs, on a circuit board evenly and mixedly, wherein a separator is also provided on the circuit board to separate UV light emitted by said UV-LEDs and illumination light emitted by said lighting LEDs, meanwhile, a controlling circuit module having a function of mode switching controls the UV-LEDs and the lighting LEDs, in such a manner that the functions of UV-LED disinfection and LED lighting are combined well in a same device, wherein the separator is a reflecting cup, in such a manner that the light emitted by the device combined by the lighting LEDs and the UV-LEDs is homogeneous and has a strong directionality, so the strong UV light does not hurt people in some situations, and the lighting LEDs in the same LED device is not hurt by the strong UV light.

2. The method of disinfection and lighting by using LEDs, as recited in claim 1, wherein in the controlling circuit module,
   a) when a lighting LED works, a UV-LED stops working;
   b) when the UV-LED works, the lighting LED stops working; and
   c) terminal SW1 outputs a certain power by a built-in circuit in an integrated chip U1, N-type diode Q1 and P-type diode Q2 are selectively electrified by time division method, in such a manner that the lighting LED and the UV-LED works alternately, wherein since gating frequency is high, naked eye is not able to perceive switching of working state of the lighting LED and the UV-LED.

3. The method of disinfection and lighting by using LEDs, as recited in claim 1, wherein the controlling circuit module further comprises a mode allowance switch MODE, for switching to a UV MODE or a LIGHT MODE, in the UV MODE, step b) or step c) is executed, and in the LIGHT MODE, only step a) is executed.

4. An LED device for implementing the method of disinfection and lighting by using LEDs, as recited in claim 1, comprising: a body, a shield, a cover, and a controlling circuit module, wherein said controlling circuit module is provided in a lower portion of said shield, said shield and a thread of said cover are provided on the body, and said LED further comprises a reflecting cup assembled on a circuit board, where LEDs are welded.

5. The LED device, as recited in claim 4, wherein said reflecting cup is in a shape similar to an inverted trapezium, said reflecting cup comprises a plurality of reflecting cellular cups provided therein, which are arranged like a honeycomb, and sizes and distributing method of said reflecting cellular cups changes according to situations.

6. The LED device, as recited in claim 4, wherein a proportion of diameters of said reflecting cellular cups in said reflecting cup is set according to an actual optical effect.

7. The LED device, as recited in claim 5, wherein a proportion of diameters of said reflecting cellular cups in said reflecting cup is set according to an actual optical effect.

8. The method of disinfection and lighting by using LEDs, as recited in claim 1, wherein the reflecting cup is in a shape of an inverted trapezium, the reflecting cup comprises a plurality of reflecting cellular cups, which are arranged in a manner of a honeycomb, the LEDs welded on the circuit board are respectively inserted into the corresponding first and second reflecting cellular cups, arranged like a honeycomb, through corresponding LED holes, wherein the reflecting cellular cups in the center have a size bigger than the reflecting cellular cups around the center have; the reflecting cellular cups around the center are same in size, in such a manner that the LEDs in same type are treated by same light distributions, and light emitted by the LEDs are homogeneous.

9. The method of disinfection and lighting by using LEDs, as recited in claim 4, wherein the reflecting cup is in a shape of an inverted trapezium, the reflecting cup comprises a plurality of reflecting cellular cups, which are arranged in a manner of a honeycomb, the LEDs welded on the circuit board are respectively inserted into the corresponding first and second reflecting cellular cups, arranged like a honeycomb, through corresponding LED holes, wherein the reflecting cellular cups in the center have a size bigger than the reflecting cellular cups around the center have; the reflecting cellular cups around the center are same in size, in such a manner that the LEDs in same type are treated by same light distributions, and light emitted by the LEDs are homogeneous.

* * * * *